United States Patent [19]

Geho et al.

[11] Patent Number: 4,705,804

[45] Date of Patent: Nov. 10, 1987

[54] DIARRHEAL ANTITOXIN

[75] Inventors: W. Blair Geho; John R. Lau; Joseph Jacob, all of Wooster, Ohio

[73] Assignee: Technology Unlimited, Inc., Wooster, Ohio

[21] Appl. No.: 730,830

[22] Filed: May 6, 1985

[51] Int. Cl.$^4$ ........................ A61K 31/34; A61K 9/70; A61K 9/42

[52] U.S. Cl. ..................................... 514/474; 424/85; 514/867

[58] Field of Search .................. 514/474, 867; 424/38, 424/28

[56] References Cited

U.S. PATENT DOCUMENTS 4,217,344  8/1980  Vanlerberghe et al. .............. 424/38
4,377,568  3/1983  Chopra ................................. 424/35

OTHER PUBLICATIONS

Klenner, "Observations on the Dose and Administration of Ascorbic Acid when Employed Beyond the Range of a Vitamin in Human Pathology" Journal of Applied Nutrition 23, 61–68, 1971.

Primary Examiner—Albert T. Meyers
Assistant Examiner—F. L. Krosnick
Attorney, Agent, or Firm—Frijouf, Rust & Pyle

[57] ABSTRACT

This disclosure teaches a method of inactivating bacterial toxins, such as produced by *Vibrio cholerae* and *Escherichia coli* (hereinafter *V. cholerae* and *E. coli*) that are responsible for diarrhea in warm-blooded animals, comprising the placing of an effective dosage of ascorbic acid salts thereof, or derivatives such as the ester ascorbyl palmitate in the intestinal tract.

Definition: Ascorbic acid, salts thereof, and derivatives thereof such as ascorbyl palmetate have been identified as suitable detoxifying material according to this invention. For the sake brevity, the term "ascorbic acid" hereinafter shall include the salts and esters.

Diarrhea as used herein will include other toxins effecting the lower duodenum and intestines.

1 Claim, No Drawings

DIARRHEAL ANTITOXIN

BACKGROUND OF THE INVENTION

1. Field of the Invention

This invention described the innovative use of L-ascorbic acid as orally applied to the gastrointestinal tract. The L-ascorbic acid counteracts the toxins known to contribute to diarrhea secondary to bacterial infection.

2. Description of Prior Art

Numerous articles have been published in medical textbooks regarding bacterial diarrhea, its symptoms and its etiology (Scientific American Medicine, Volume 7, No. 6).

The following background information, substantially as set forth in Merck Manual 13th Edition, Chapter 12, page 788, will assist in understanding the discovery of this invention:

Etiology

Gastroenteritis is a generic term, often implying a non-specific, uncertain, or unknown etiology. However, certain diseases of known bacterial, viral, parasitic, or toxic etiology can also be included in the clinical definition. Indeed, when a specific etiology can be identified, the less specific term (gastroenteritis) can be avoided. Such bacterial dysenteries as cholerae, salmonellosis, and shigellosis share common pathologic mechanisms and can be considered prototypes for syndromes of lesser specificity.

Pathophysiology

Certain bacterial species elaborate exotoxins (enterotoxins) which impair intestinal absorption and can provoke secretion of electrolytes and water. In some instances, such as the enterotoxin of V. cholerae, a chemically pure toxin has been characterized. Pure toxin alone will produce a voluminous watery secretion from the small intestine seen clinically, thereby demonstrating an adequate pathogenic mechanism for the diarrhea. Interotoxins probably explain other diarrhea syndromes previously attributed to non-specific causes. For example, E. coli toxins has been determined to be the cause of some outbreaks of "nursery diarrhea" and "traveler's diarrhea". Non-cholera vibrosis elaborates a toxin which appears to be responsible for some types of food poisoning due to shellfish.

In addition to the above substantially quoted background, the literature notes that some shigella, salmonella and even E. coli species penetrate the mucosa of the small bowel or colon and produce microscopic ulceration, bleeding, exudation of protein-rich fluid and secretion of electrolytes and water. This may occur whether or not the organism elaborates a toxin. This invention is directed to the prevention and/or treatment of those types of diarrhea caused by toxins.

Traveler's diarrhea syndrome causes wide spread difficulty for travelers, especially in underdeveloped parts of the world. The pathogenic strain of E. coli is endemic to the parts of the world that lack the hygienic facilities of the United States and countries of Western Europe. Specific therapy for preventing this syndrome has been lacking, and only symptomatic anti-diarrheal therapy has been available.

SUMMARY OF THE INVENTION

This invention is the discovery that L-ascorbic acid, salts thereof, or derivatives such as the ester ascorbyl palmitate when applied to the gastrointestinal tract of humans and other warm-blooded animals, will inactivate toxins that contribute to traveler's diarrhea.

Although the toxin which is responsible for traveler's diarrhea is essentially that produced by certain strains of pathogenic E. coli., there are other toxins produced by other bacteria which are essentially identical from chemical and biological points of view (i.e. cholerae toxin produced by V. cholerae).

The novel discovery and approach of this invention is the focus on detoxification of the toxic product of bacteria, at the location of the toxin, rather than an attempt to eliminate the bacteria.

It has been discovered, according to this invention, that L-ascorbic acid is outstandingly effective in detoxification of the toxins found in the instestinal tract of a human host. Although L-ascorbic acid is known to be a strong antioxidant, it is not known how the L-ascorbic acid inactivates the toxin. Toxin structures are as yet unknown, and the chemistry of this invention is unknown.

It is known by the discovery of this invention that the external administration of an effective amount of ascorbic acid throughout the lumen of the small intestine and large intestine of a human host prior to and during exposure to toxin producing bacteria will detoxify any toxins to the point of substantially complete elimination of the danger of traveler's diarrhea and similar toxin induced distress.

GENERAL DISCLOSURE

This disclosure explains the discovery that the toxins which cause diarrhea are inactivated by L-ascorbic acid and its salts. The L-ascorbic acid is administered orally as a product which is intended for use in preventing and/or treating diarrhea. The invention also describes the need for pharmaceutical forms of ascorbic acid that remain within the lumen of the gut and are not systematically absorbed. In order for ascorbic acid to be effective, it must inactivate the causative toxins at the location of the toxin which is the lumen of the gut, especially the lower duodenum, ileum and jejunum. Free ascorbic acid administered orally in all available dose forms, either as free ascorbic acid, or its salts or derivative or in sustained release form, is inadequate as an antitoxin because it is rapidly absorbed from the stomach and upper duodenum.

This invention discloses a means to specifically inactivate the causative bacterial toxins by a chemical reaction. The chemical reaction utilizes forms of L-ascorbic acid that are active in the small intestine. This invention is useful both as a prophylactic and therapeutic means to treat traveler's diarrhea and cholerae.

DESCRIPTION OF THE PREFERRED EMBODIMENT

L-ascorbic acid has important properties in that the dry crystals are stable in the air for a very long period of time. However, once L-ascorbic acid enters into solution, it is capable of undergoing oxidation in a variety of reactions. The tendency of L-ascorbic acid to be oxidized increases with increasing pH ("The antioxidant Vitamins," CRC Critical Review, *Food Sciences and Nutrition*, March, 1979, pp. 271).

L-ascorbic acid is added, according to this invention, to an appropriate carrier at milligram levels, which is completely compatible with the pH of the intestinal tract.

Although it has not been determined how L-ascorbic acid functions to detoxify bacterial toxins, it is known that L-ascorbic acid possesses relatively strong reducing power as is shown in its ability to decolorize many dyes (*Merck Index*, 8th ed.). These kinds of reactions may be accelerated by alkalies, iron and copper.

There appears to be no known approach to traveler's diarrhea prevention using L-ascrobic acid. This new use of a very safe product has been discovered, according to this invention, to possess essentially full and complete power for inactivation of toxins responsible for traveler's diarrhea.

EXAMPLE A

The mechanism by which L-ascorbic acid renders the *E. coli* and cholera toxins ineffective is unknown, but L-ascorbic acid will act as a reducing agent, an antioxidant and a free radical sequestering agent. From in vitro testing of this invention it has been shown that ascorbic acid does inactivate the causative agents in traveler's diarrhea. L-ascorbic acid is known to oxidize to dehydroascorbate. Therefore, it is theorized that the detoxification may be the result of the following reaction:

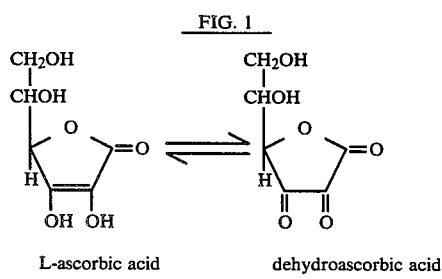

L-ascorbic acid      dehydroascorbic acid

By a series of intermediate reaction steps, a protein or toxin may interact with the ascorbic acid and any intermediates to break the disulphide bond and produce reduced sulfhydral groups. The reaction is represented as follows:

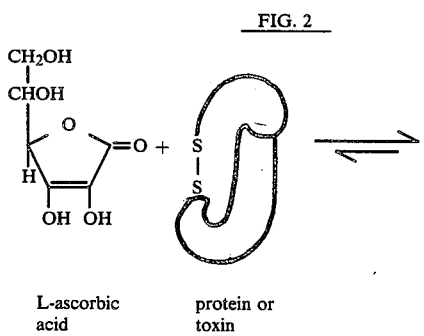

L-ascorbic acid     protein or toxin

-continued
FIG. 2

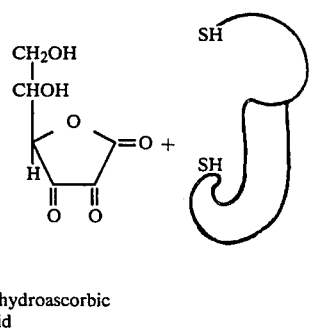

dehydroascorbic acid

It is necessary to emphasize that this invention is a discovery, and that the actual mechanism of detoxification is not yet known.

EXAMPLE B

The efficacy of the ascorbic acid in detoxifying bacterial toxins is demonstrated in an animal model. The ascorbic acid is supplied via a surgically implanted catheter to the region of the intestine which is susceptible to toxin action. Two different animals (i.e. rabbits) are used, one for receiving toxin alone and the other toxin plus ascorbic acid. The dose of Cholera Toxin is 20 $\mu$g/kg and the dose of ascorbic acid is 10 mg/kg. Both agents are admininstrated in pH 6.5 phosphate buffered saline. The control rabbit received only toxin and the treatment rabbit received both toxin and ascorbic acid. The control rabbit exhibited the classical diarrhea symptoms while the treatment rabbit was unaffected by the toxin.

In the preceding disclosure, there has been no reference to catalytic agents, and, in fact, catalytic agents are believed to be unnecessary in most instances. There are sufficient metallic ions present in most environmental situations to serve any catalytic requirements of the oxidation of L-ascorbic acid. Nevertheless, in order to assure completion of the test results, and in actual commerical use, it is recommended that some additional cupric++ ion or ferric ion be provided in order to assure a complete reaction sequence.

Again, there are many possible and unknown reactions of L-ascorbic acid and toxins, but from a careful review of the observed action according to this invention, and from extensive theoretical studies, the above effect is probably at least one of the major reactions taking place in this invention. In this reaction sequence, ascorbic acid is the reductant, and the cupric++ ion is the pro-oxidant which illustrates the reaction. The cupric++ ion is reduced to the cuprous+ ion (Cu+), along with molecular oxygen. For each molecule of ascorbic acid that is oxidized to dehydroascorbate, a molecule of hydrogen peroxide is liberated. Hydrogen peroxide is a powerful oxidant when in the presence of cuprous+ ion and is capable of generating hydroxyl radicals according to the reaction below:

$$Cu^+ - 1e^- + H_2O_2 \rightarrow Cu^{++} + OH + HO^-$$

On the product side of the equation, the hydroxyl free radical (OH) that is formed is very reactive and is known to participate in reactions that irreversibly inactivate proteins. It is recognized that a variety of metals found in trace quantities in biological systems, as well as water supplies, may help facilitate the toxin inactivation reactions by ascorbic acid. While the cupric ion reactions are illustrated above, no special exclusivity should be assigned to the cupric ion, since this transition series metal should be substituted by a variety of metals occurring in trace amounts in biological systems.

Additional Studies with the Ascorbic Acid Antitoxin

The efficacy and specificity of ascorbic acid as an antitoxin has been tested in a rabbit model according to test procedures by John Craig. "Serological Evidence for the Identity of Vascular Permeability Factor and Ileial Loop Toxin V. Cholera," *Journal of Infectious Diseases,* Vol. 121, No. 3, 1970, pp. 242,250.) This model has been used extensively since its discovery to study the mode of action of bacterial toxins. It has also been used to evaluate the means by which toxin activity can be inactivated. This test involves injecting minute amounts of toxin into the shaved skin of rabbits. The action of toxins is to increase the capillary permeability of the skin, producing a localized edema. This edema is visualized as a wheel of 5–10 mm in diameter. The vascular leakage is made more apparent by injecting a blue dye (i.e. Evans blue) intravenously. As a result, the dye leaks out of the capillaries whose permeability has been increased by the toxin. The size of the blue spot in the skin is an indicator of the toxin's presence and activity in altering capillary permeability.

The experimental procedure is essentially that described by Craig. The borate-gel buffer described can be replaced by phosphate buffered saline (40 mM), at pH 7.0–7.5. Cholera toxin was chosen from a variety of toxins as the representative toxin for study. Cholera toxin and *E. coli* toxin are regarded as chemically similar. The amount of cholera toxin found to elicit the vascular leakage in the skin was 1 to 5 ng/0.1 ml of the phosphate buffered saline or borate gel. L-ascorbic acid, when mixed with the toxin, was effective in blocking the toxins' deleterious action. L-ascorbic acid was added in the dose range of 0.001 to 0.1 $\mu$ Mole per 0.1 ml of toxin (1–5 ng). Transition metals, such as CuII and FeIII are thought to be required in trace amounts. Since trace amounts of transition metals are found in biological fluids (i.e. extracellular fluid), the addition of these trace metals was not necessary. High levels of metals, i.e. millimolar range, are toxic to biological systems and should not be used. The specificity of the antitoxin was studied, substituting pyruvic acid and malic acid for the ascorbic acid. Neither pyruvic acid nor malic acid was effective an antitoxin at even the highest dose (1 mg/ml) used.

The rabbit skin model has been shown to be predictive of bacterial toxin activity for many years. It is concluded from the above data that L-ascorbic acid and its salts are effective and specific antitoxin materials. Other similar organic acids, such as pyruvic and malic acids, are not effective as antitoxins.

EXAMPLE C

Using a rabbit model, the rabbits were properly prepared for surgery, then opened to expose the intestines. Several segments of intestines were created by suturing at spaced intervals. This procedure isolated the segments, but otherwise provided a short term normal function.

Into one segment was injected the toxin of *E. coli.* Into a separate segment was injected the resultant of a mixture of the same toxin incubated one hour with ascorbic acid.

The rabbits were closed for 24 hours, and when reopened, it was observed that the segments with toxin were expanded by fluids, but those segments with the incubated ascorbic acid were unaffected.

Hence, it is reaffirmed that introduction of ascorbic acid, salts thereof, or derivatives such as ascorbyl palmetate if introduced to the lower duedenum by any means, will effectively eliminate the otherwise deleterious effects of toxins provided by various elaborating bacteria.

EXAMPLE D

Further studies of the effects of Vitamin C on cholera enterotoxin have been made, using the rabbit skin vascular permeability assay as originally described by Dr. John P. Craig (supra). The structure of the *E. coli.* enterotoxin is very similar to that of cholera enterotoxin, its mode of action appears to be identical, and its effect on vascular permeability of rabbit skin is identical.

The study to-date has indicated that when the cholera enterotoxin in a does of 5 microgram/ml is incubated for one hour with 1 milligram per liter of ascorbic acid prior to intradermal injection in the rabbit skin, the size of the lesion (as determined by the diameter of the lumen area which develops after intravenous injection of dye, according to the technique of Craig) is reduced by 40%. Control areas in the same animal, in which borate-gelatin buffer control was injected into the skin, were entirely negative both with and without ascorbic acid.

EXAMPLE E

In order to place the ascorbate into position to serve as an effective antitoxin, it must be placed in the area where lesions may form at the time toxins are known to form. Accordingly, it is desirable to place the crystalline form of the ascorbate in a drug carrier device that may reside in the intestinal tract in the area colonized by pathogenic *E. coli* or *V. cholerae.* Enteric coated time-release dose forms that release the ascorbate throughout the length of the small intestine are adequate. The typical dose of ascorbate should range from 15–100 mg/kg body weight.

The foregoing theory of the action of ascorbic acid forms will provide the best available guide to those using and prescribing this means of avoiding the discomfort and danger of toxic diarrhea. Whether the theory is later confirmed, modified, or overturned, it remains that this invention is in the discovery that ascorbic acid, delivered to the lumen of the gut, by any means available prior to invasion of bacteria that elaborate toxins, will eliminate the toxin and its deleterious effect on the human system.

This invention directs the placement of ascorbic acid in the lumen of the gut whenever one suspects that exposure to toxin elaborating bacteria may be encountered.

EXAMPLE F

Ascorbic acid formulated into a non-absorbable form remains within the lumen of the gut and remains available to carry out the deactivation of bacterial toxins. The preferred method is to use ascorbyl palmitate as a component in a liposome. The procedure is as follows:

(1) Form the lipid crust (a) dissolve 20 mg ascorbyl palmitate 60 mg distearoyl lecithin 10 mg cholesterol in 10 ml chloroform: methanol (2:1 v/v).

(b) evaporate solvent to dryness with rotoevaporator at 60° C.

(2) Add 20 ml saline to lipid crust and sonicate at high setting, using a Heat Systems Sonifier and Branson Cuphorn for 10 minutes at 60° C.

(3) Anneal 10 minutes at 60° C.

The product is a mixture of liposomes (small to large - unilamellar to multilamellar) that are suitable for oral administration either as a liquid suspension or freeze-dried product in capsules.

A typical dose is 0.2 ml per kg body weight with a range of 0.05 to 1.0 ml being acceptable.

The product has reactive ascorbate on the surface as well as within the liposomal layers. The product remains primarily within the lumen of the gut and detoxifies the bacterial toxins without killing organisms.

The available literature does not provide any suggestion of ascorbic acid forms which deliver the ascorbic acid in therapeutic strength to the lower intestine. There is no known product or literature suggesting need for such forms of ascorbic acid.

Ascorbic acid in time-release units is available. This time-release form is intended to be taken into the blood stream over an extended time period by absorption from the stomach and duodenum. It is not apparent that the ascorbic acid need be delivered to the lower intestine, and in fact, little would be absorbed from the lower intestine if some of the units were found intact therein. Therefore, according to the intent of timerelease of ascorbic acid, any yet intact in the lower intestine is wasted.

This invention provides full dosage of the ascorbic acid into the lower portion of the duodenum and the intestine. None is intended to be absorbed in the stomach or upper duodenum.

What is claimed:

1. The method of eliminating diarrhea caused by the toxins produced by *V.Cholera* or *E. Coli* by the oral administration of an antitoxin effective amount of ascorbic acid or ascorbyl palmitate whereby ascorbic acid or ascorbyl palmitate is present throughout the lumen of the small and large intestine in a detoxifying amount without killing said organisms.

* * * * *